United States Patent [19]

Blöcker

[11] Patent Number: 5,763,227

[45] Date of Patent: Jun. 9, 1998

[54] PROCESS FOR THE PRODUCTION OF PRIMERS AND TEMPLATE BANK THEREFOR

[75] Inventor: Helmut Blöcker, Braunschweig, Germany

[73] Assignee: Gesellschaft fur Biotechnologische Forschung mbH (GBF), Braunschweig, Germany

[21] Appl. No.: 635,964

[22] PCT Filed: Oct. 28, 1994

[86] PCT No.: PCT/EP94/03547

§ 371 Date: Apr. 29, 1996

§ 102(e) Date: Apr. 29, 1996

[87] PCT Pub. No.: WO95/11970

PCT Pub. Date: May 4, 1995

[30] Foreign Application Priority Data

Oct. 28, 1993 [DE] Germany ............... 43 36 911.1

[51] Int. Cl.⁶ ............... C12P 19/34; C12Q 1/68; C07H 21/02
[52] U.S. Cl. ............... 435/91.1; 435/6; 536/23.1
[58] Field of Search ............... 435/6, 91.1; 935/77, 935/78; 536/23.1

[56] References Cited

FOREIGN PATENT DOCUMENTS 8911211  11/1989  WIPO.

OTHER PUBLICATIONS

Khrapko et al, FEB 256(1,2): 118–122 (1989).
Szybalski et al, Gene 90: 177–178 (1990).

*Primary Examiner*—Eggerton A. Campbell
*Attorney, Agent, or Firm*—Kane, Dalsimer, Sullivan, Kurucz, Levy, Eisele and Richard

[57] ABSTRACT

The invention relates to a process for the production of a primer for consecutive DNA sequencing, in which at least two shortmers are hybridised adjacent to one another using a template and are then ligated with one another to form the primer, the process being characterised in that (a) a template in the form of a single strand of nucleotides is used in which the number of nucleotides is at least 6 and is not greater than approximately twice the total number of nucleotides of all the shortmers used, and (b) the primer formed is then separated from the template and from unreacted shortmers and recovered. The invention relates also to banks (libraries) of templates for the mentioned process.

17 Claims, 8 Drawing Sheets

PROCESS FOR THE PRODUCTION OF PRIMERS AND TEMPLATE BANK THEREFOR

This application is a 371 of PCT/EP94/03547, filed on Oct. 28, 1994.

BACKGROUND OF THE INVENTION

1. Field of the Invention

The invention relates to the sequencing of deoxyribonucleic acid.

2. Brief Description of the Related Art

The methods used for DNA sequencing today are mainly the Maxam-Gilbert technique and the Sanger method. In the Sanger method, the DNA to be sequenced—single-stranded DNA, or DNA that has been made single-stranded—is polymerised enzymatically to form a double strand. For that purpose, a short region of the DNA first has to be made double-stranded, since DNA polymerases need a short double-stranded region having a free 3'-hydroxyl end for the incorporation of nucleotides (template/primer dependency of the enzymatically catalysed incorporation of nucleotides). According to the shortmer concept (EP-B-89 906 358.0), the short double-stranded region is synthesised by hybridising two or more shortmers adjacent to one another on, as template, the single-stranded DNA to be sequenced, and then binding or ligating the shortmers together to form a primer. Starting from the short double-stranded region, the DNA strand to be sequenced is then successively enzymatically complemented with DNA polymerase. As soon as the whole sequence has been read in order to evaluate the analysis, a primer attachment site at the 3' end of the DNA sequence just read is again selected for the next sequencing operation. Shortmers are again hybridised and ligated at that primer attachment site. The new primer is used for subsequent sequencing.

On the one hand, primers that are as long as possible are of interest, in order to enable a DNA strand that is to be sequenced to be addressed individually using such a primer. On the other hand, the size of the shortmer banks to be used for the production of the primers increases dramatically as the primer length increases. It has been found, however, that it is possible for DNA strands that are to be sequenced to be added sufficiently accurately with primers from 12 to 18 nucleotides in length.

In addition, it has been found that the classic shortmer concept is incapable of improvement in the following respect: high-value sequencing protocols start from an excess of primer over the DNA strand to be sequenced. If the primer is present in a ratio of 1:1 or less with respect to the DNA strand to be sequenced, then, in experiments, the reading distances observed are generally shorter than would be expected with an excess of primer. If, accordingly, in the case of the shortmer concept hybridisation and ligation are carried out once only and the primer ligation product is not melted off and then hybridised and ligated again, then at the very most a 1:1 stoichiometry of primer to DNA strand to be sequenced is achieved, despite the presence or an excess of the shortmer used.

SUMMARY OF THE INVENTION

That prior art can now be improved in accordance with an embodiment of the invention by means of a process for the production of a primer for consecutive DNA sequencing, in which at least two shortmers are hybridised adjacent to one another using a template and are then ligated with one another to form the primer, the process being characterised in that (a) a template in the form of a single strand of nucleotides is used in which the number of nucleotides is at least 6 and is not greater than approximately twice the total number of nucleotides of all the shortmers used, and (b) the primer formed is then separated from the template and from unreacted shortmers and recovered.

Primer: By "primer" there is to be understood in the present context a short strand of DNA with the aid of which the DNA strand to be sequenced is made double-stranded over a correspondingly short region.

Template: In contrast to the DNA strand that is to be sequenced, there is to be understood by "template" in the present context a single strand of nucleotides on which a primer can be produced, which primer is used for the sequencing of a DNA strand only after it has been separated from the template.

Shortmer: There are to be understood by "shortmers" oligonucleotides that can be ligated to form a primer; cf. EP-B-89 906 358.0.

BRIEF DESCRIPTION OF THE DRAWINGS

FIGS. 1 to 4 depict a sequencing of M13 mp18 (R), i.e. an oligonucleotide. The sequencing is carried out with a commercial primer (Universal Primer=UP). The signals of the four different nucleotides A, C, G and T are represented by four different curves. As can be drawn from FIG. 4, the sequencing was carried out up to nucleotide 541. FIG. 5 to 8 show a comparative sequencing of the same oligonucleotide and a ligated primer according to the invention, i. e. P9. Sequencing could be carried out to nucleotide 491.

DETAILED DESCRIPTION OF THE INVENTION

Figure 1A:
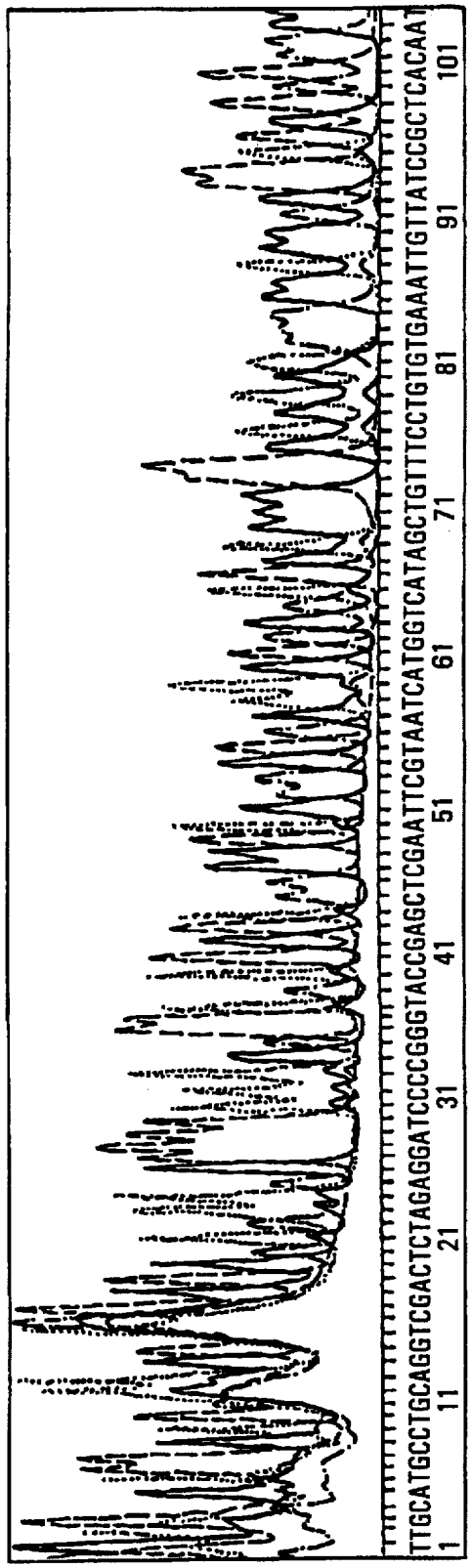

According to the invention, therefore, the binding or ligation of the shortmers is carried out on templates in accordance with the shortmer concept, the templates being at least partially complementary to the shortmers used. The templates may be short strands that have been produced synthetically from nucleotides. It goes without saying that it is possible to use for those syntheses not only the four nucleotides bases for A, C, G and T, of which natural DNA is composed, but also derivatives, provided that there is at least partial complementarity with the shortmers. For the prior art, references is made to DE-A-3 501 306, FR-A-2 190 505, U.S. Pat. No. 4,988,617, WO-A-86/06 413, WO-A-91/09 623 and WO-A-91/17 239. In order to produce a derivatised or degenerate template, it is possible, for examples for inosine or a mixture of the four nucleotide bases A, C, G and T to be used for incorporation at the same template position.

In the same way, the shortmers may be short strands that have been produced synthetically from nucleotides. Again it goes without saying that it is possible to use for those syntheses not only the four nucleotide bases for A, C, G and T, of which natural DNA is composed, but also derivatives, provided that there is at least partial complementarity with the template. The statements made above regarding templates apply correspondingly.

According to the invention and in accordance with the prior art, one of the nucleotide bases may also be labelled, for example radioactively or fluorescently, especially for the 3' end or the 5' end.

According to the invention, one of the nucleotide bases may also carry a radical for facilitating separation of the template, for example it biotin radical.

According to the invention, it is also possible for a modified nucleotide base having exclusive complementarity to be provided at at least one site on a template, in order, for example, to raise the melting temperature of primers that have been formed.

According to the invention, the first shortmer may also be provided on a solid phase. In stage (b) mentioned above, the template and the subsequent shorter or shortmers, which were not provided on a solid phase, are then separated off.

According to the invention, the number of nucleotides in the template can be smaller by up to approximately the number of nucleotides in one of the shortmers used, or larger by up to approximately the number of nucleotides in one of the shortmers used, than the total number of nucleotides in all the shortmers used.

According to the invention, the number of nucleotides in the template may correspond approximately to the total number of nucleotides in all the shortmers used.

According to the invention, 6-mers, 7-mers, 8-mers and/ or 9-mers are preferably used as shortmers.

Preference is given according to the invention to the use of two shortmers, it being possible for the number of nucleotides in the template to be from 8 to 18.

According to the invention, two shortmers (a) from a bank of 6-mers and/or 7-mers and/or (b) from a bank of 8-mers and/or 9-mers can be used and, in the case of (a) and/or (b), an 8-mer or a 9-mer from a bank according to (b) can be used as template.

If a 5-mer is used as shortmer for the formation of the primer, it is advantageous for the 5-mer to be used with at least one shortmer from the group of the 7-mers, 8-mers or 9-mers.

The process according to the invention therefore offers the advantage that, in a sequencing operation, sufficient ligation product can be used for a favourable primer excess to be produced, i.e. a ratio of primer to DNA strand to be sequenced of $\geq 1:1$.

According to a further embodiment of the invention, a bank (library) of templates is provided that are suitable for the production of primers for consecutive DNA sequencing, two, three, four or more shortmers being hybridised adjacent to one another, using a template from the bank, to produce the primer, the hybridised shortmers then being ligated to form the primer and the primer formed then being separated from the template and from unreacted shortmers and recovered, from at least one to a maximum of all of the nucleotides in from at least one template to all the templates in the bank having a complementarity similar to at least two of the four natural nucleotide bases, with the proviso that the total number of all conceivably or theoretically possible templates in the bank does not in practice exceed the total number of all shortmers conceivably possible for the production of the primer.

In order to avoid pursuing the shortmer concept to the point of absurdity, it is not the aim of the invention to provide a short template for every shortmer pair or every shortmer combination. Rather, the complexity of the production of short templates is reduced by the incorporation of nucleotides having a complementarity similar to at least two of the four natural bases at one position or at individual positions of one, several or all of the templates in a bank according to the invention. In accordance with a special embodiment of the invention, inosine may be provided for that purpose as a nucleotide having a complementarity similar to at least so of the four natural nucleotide bases.

A bank according to the invention may comprise up to $4^9$ 10-, 11-, 12-, 13-, 14-, 15-, 16-, 17- or 18-mers. According to the invention, oligomers having up to 18 nucleotides that are capable of forming Watson-Crick base pairs with the shortmers are also included.

The problem underlying the invention is solved, furthermore, in accordance with a further embodiment by a bank (library) of templates that are suitable for the production of primers for consecutive DNA sequencing, two, three, four or more shortmers being hybridised adjacent to one another, using a template from the bank, to produce the primer, the hybridised shortmers then being ligated to form the primer and the primer formed then being separated from the template and from unreacted shortmers and recovered, the bank comprising from one mixture to several mixtures of templates, from two to four different bases complementary to the four natural bases being provided at one or at several positions of each of the templates of a mixture, with the proviso that the total number of all conceivably possible template mixtures, including templates from the bank that are not present in a mixture, does not in practice exceed the total number of all shortmers conceivably possible for the production of the primer.

Again, a short template is not provided for every shortmer pair or every shortmer combination, in order to avoid taking the shortmer concept to the point of absurdity. Rather, the complexity of the production of short templates is reduced in this embodiment by the incorporation of more than one nucleotide at individual template positions in a template of a given length or of a given number of nucleotide bases.

Thus a bank (library) according to the invention may comprise up to $4^9$ mixtures of 10-, 11-, 12-, 13-, 14-, 15-, 16-, 17- or 18-mers, including 10-, 11-, 12-, 13-, 14-, 15-, 16-, 17- or 18-mers that are not present in a mixture. According to the invention, oligomers having up to 18 nucleotides that are capable of forming Watson-Crick base pairs with the shortmers are also included.

The statements made above in respect of the process regarding templates having bases that are derivatised or labelled or bases that carry radicals and that facilitate separation apply correspondingly. If the first shortmer is provided on a solid phase, then again when the primer, template and unreacted shortmers are separated, the subsequent shortmer or shortmers, which were not provided on a solid phase, are separated off.

The invention is explain in more detail below by means of an experiment, with 3 Appendices and 8 Figures.

Shorter Experiment

Oligonucleotides used in the experiment (I=inosine)

F-oligo: 5' F-AAAACGAC 3'
P-oligo: 5' P-GGCCAGTG 3'
B-oligo: 5' B-IIIGGCCGTCGIII 3'
K-oligo: 5' F-CGACGTTGTAAAACGACGGCCAGT 3'

In a typical experiment, 2.2 µl (220 pmol) of a solution of a 5'-fluorescein-labelled octanucleotide (F-oligo) were combined with 4.1 µl (220 pmol) of a solution of a 5-phosphorylated oligonucleotide (P-oligo) and with 1.5 µl (150 pmol) of a 5'-biotin-labelled oligonucleotide (B-oligo) and with 4.2 µof T4-DNA ligase buffer (Gibco) and with 4 µof ATP solution (10 mM) in a 0.5 ml reaction vessel. In a programmable heating unit, the vessel containing the mixed components was heated to 80° C. within 2 minutes, maintained at that temperature for 2 minutes and then cooled to 10° C. within 20 minutes. At the start of the ligation reaction, 4 µl of T4-DNA ligase (4 units, Gibco) were added to the solution and the reaction mixture was maintained at 10° C. for a further 2 hours. Then 20 µl of Stopp-Mix (Pharmacia) were added to the solution.

For analytical monitoring, 3 µl of Stopp-Mix were added to 3µl of an aqueous dilution (1 ad 1000) of the above final solution, which was then subjected to gel electrophoresis on an 18% denaturing polyacrylamide gel in a commercial DNA sequencer (A.L.F.; Pharmacia) (1500 V, 50° C. 34 W. 38 mA, 180 min.). The automatically collected raw data were evaluated in respect of the ligation yield using the Fragment Manager programme (Pharmacia) (Appendix 1).

5 µl of water and then 100 µl of a freshly mixed suspension of Dynabeads M-280 Streptavidin (Dynal) were added to 20 µl of the above final ligation solution which was then shaken at room temperature for 15 minutes. The phase were separated using a magneta. The liquid phase was transferred to another reaction vessel and then subjected to analytical monitoring as described above (Appendix 2). The solid phase was suspended in 10 µl of 0.1N NaOH and shaken at room temperature for 15 minutes. The phases were again separated using a magnet. The liquid phase was neutralised by the addition of a maximum of 10 µl of 0.1N HCl. In several tests, the solution, of which there was barely 20 µl, contained approx. from 60 to 90% of the theoretically achievable 75 pmol of ligated and 5'-fluorescein-labelled primer. The solution was subjected to analytical monitoring as described above (Appendix 3).

The ligated printer was used in DNA sequence analyses in accordance with commercially available protocols.

Figure 1B:
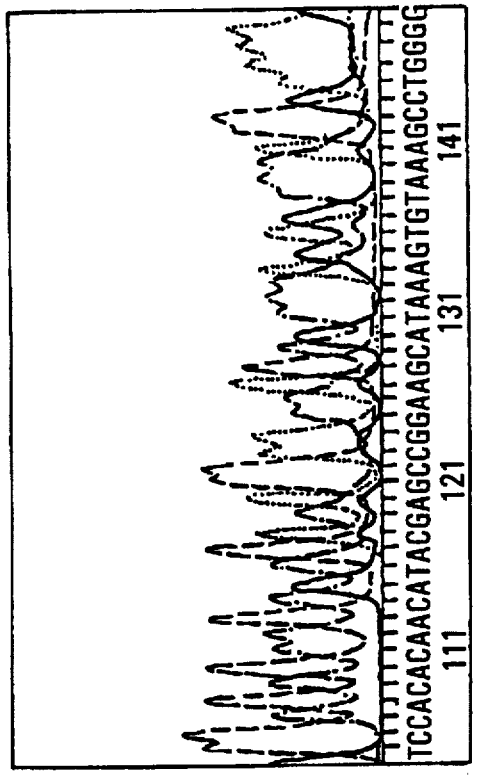
Figure 1C:
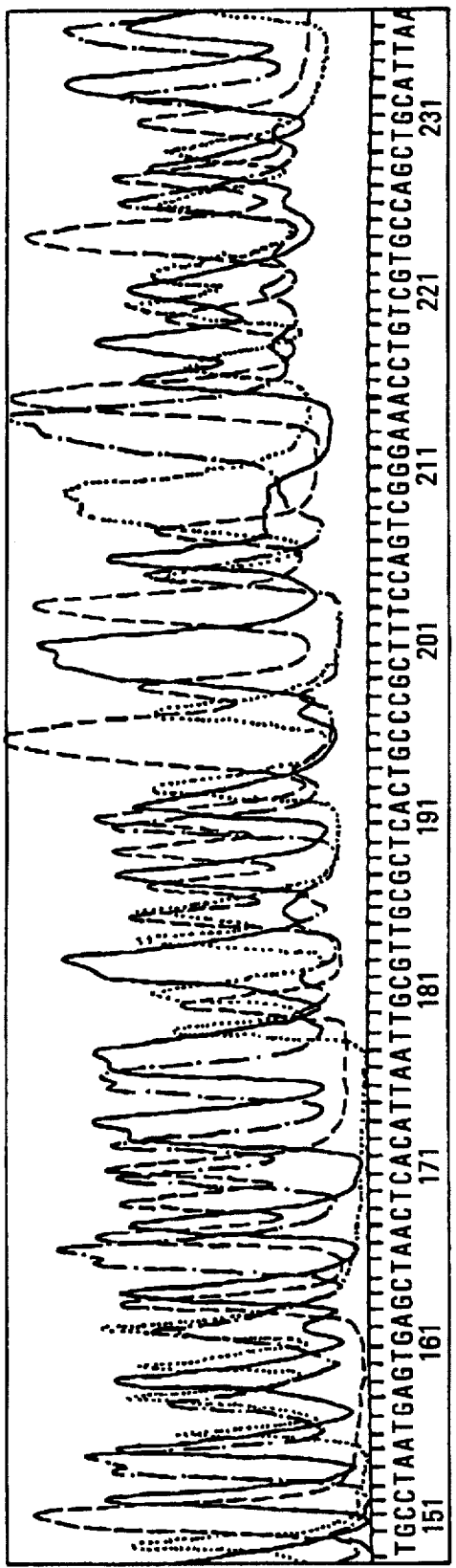
Figure 1D:
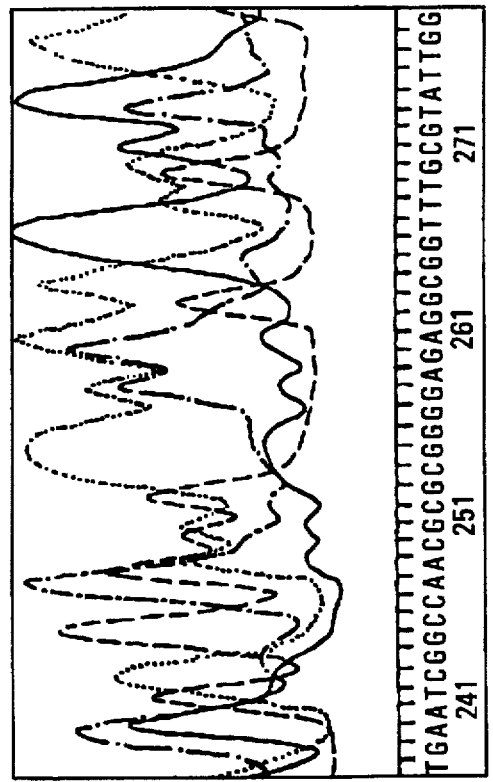
Figure 1E:
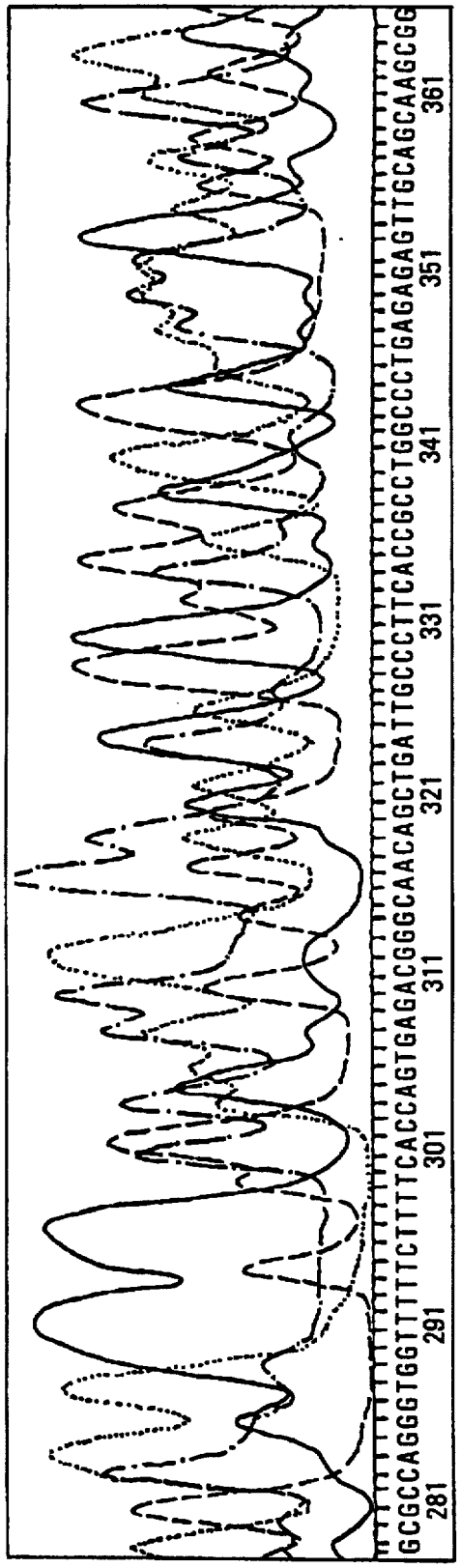
Figure 1F:
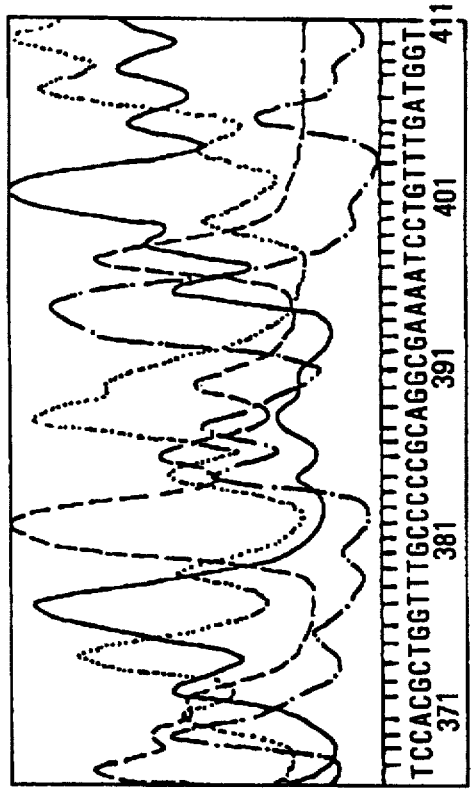
Figure 1G:
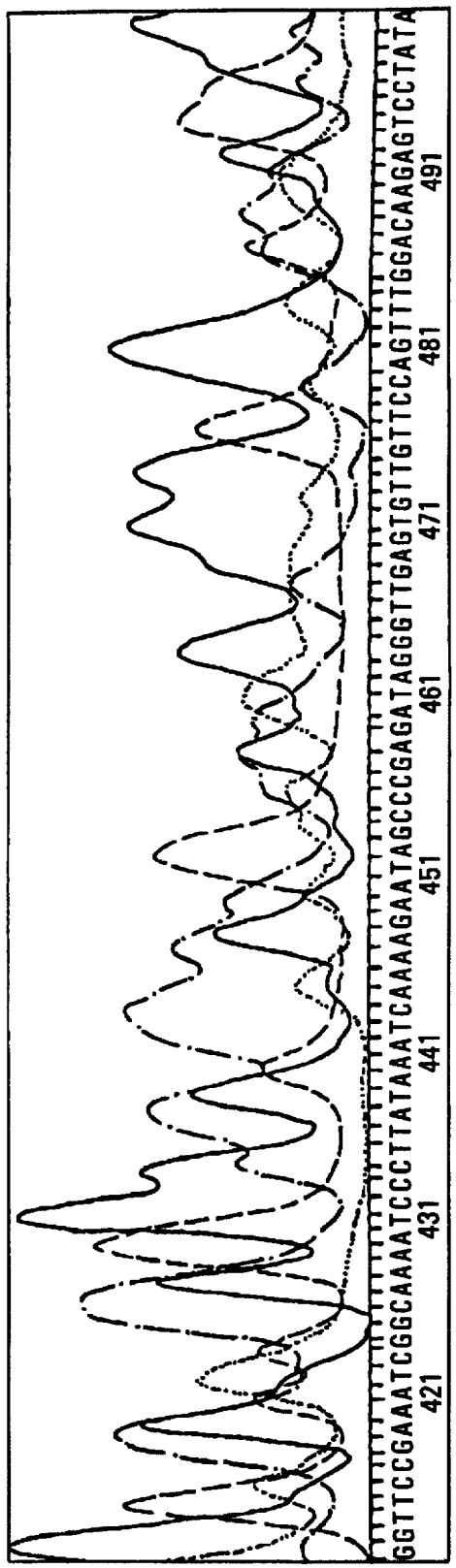
Figure 1H:
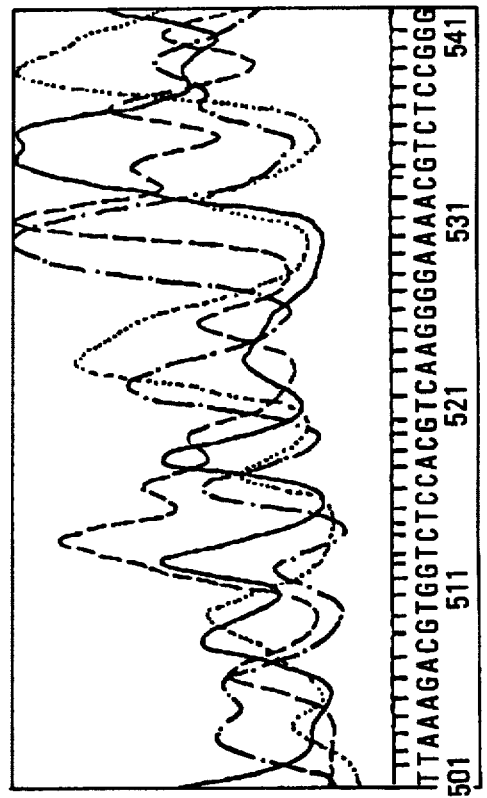
Figure 2A:
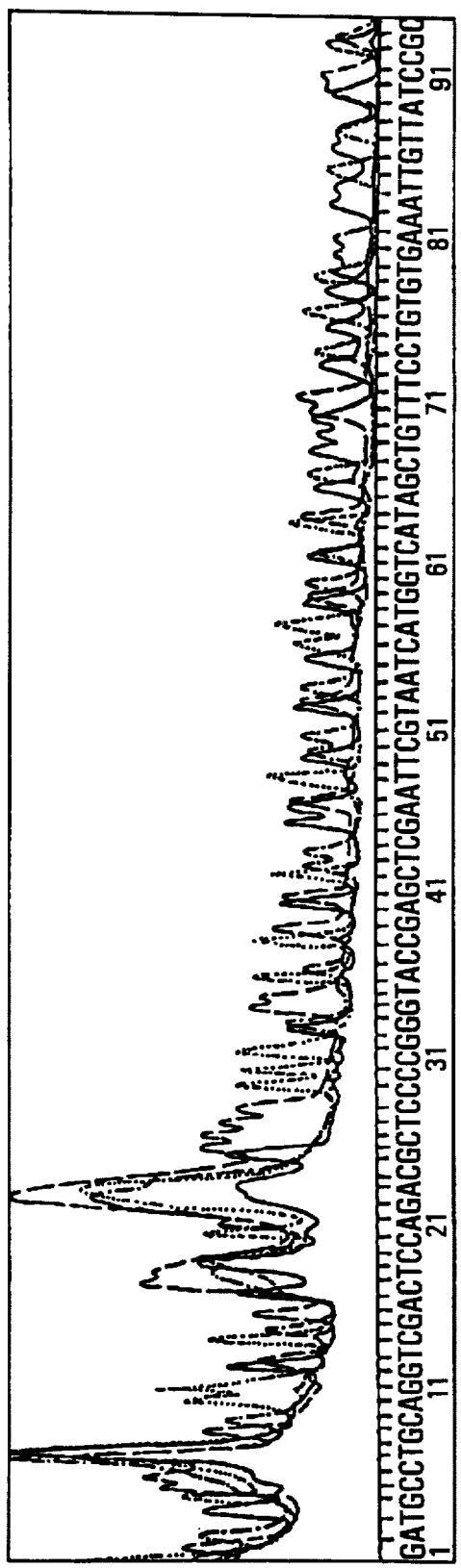
Figure 2B:
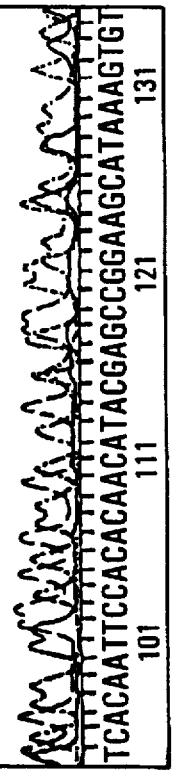
Figure 2C:
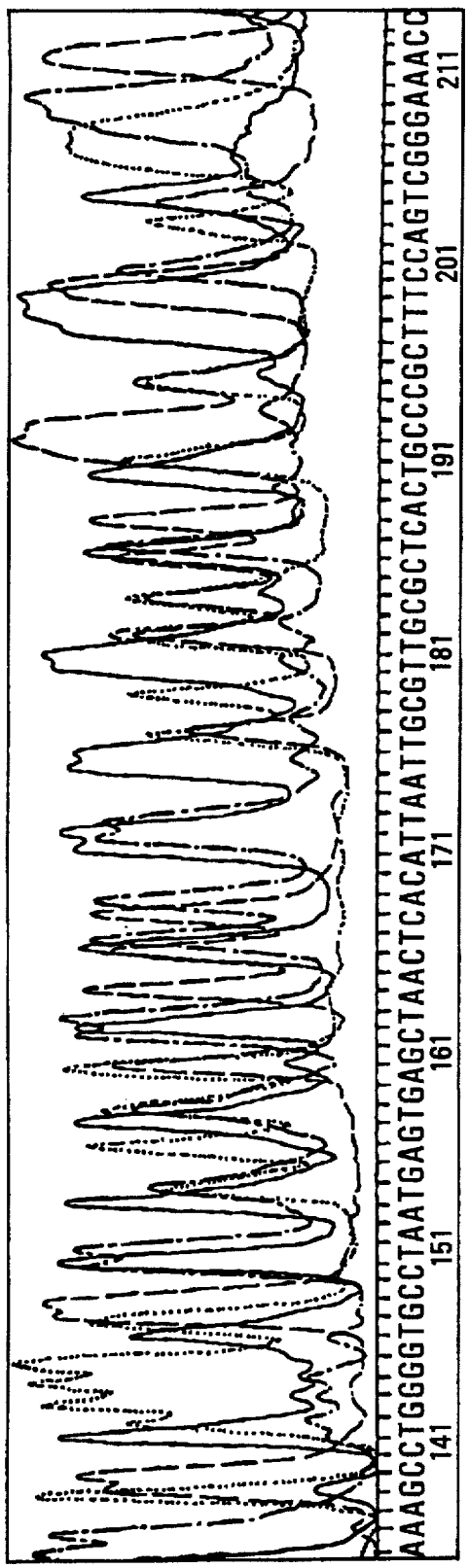
Figure 2D:
Figure 2E:
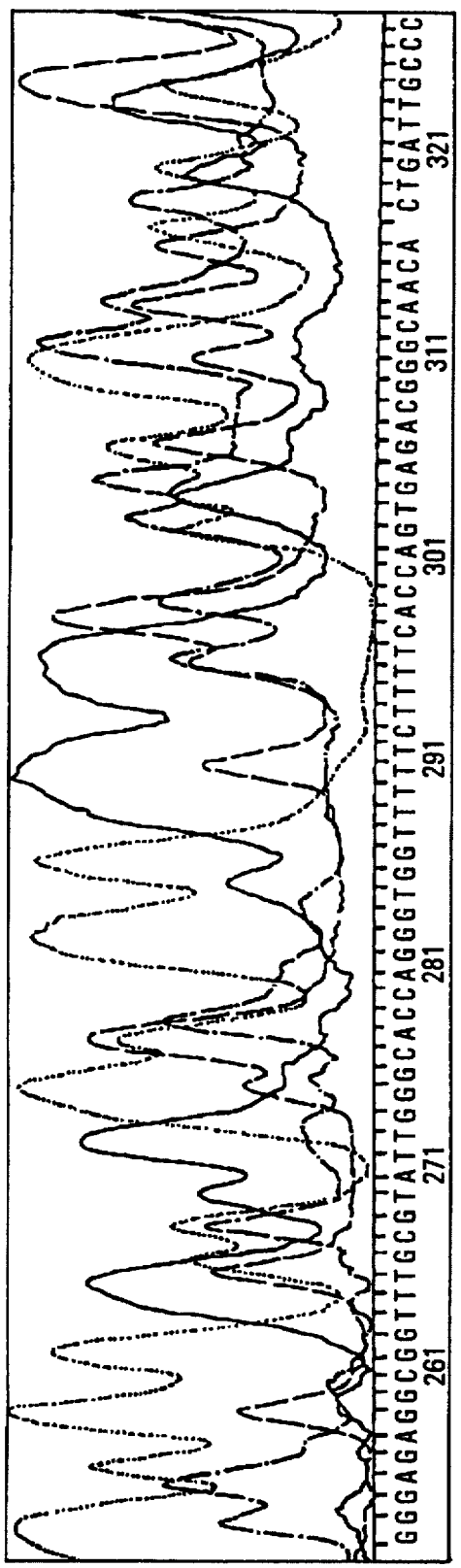
Figure 2F:
Figure 2G:
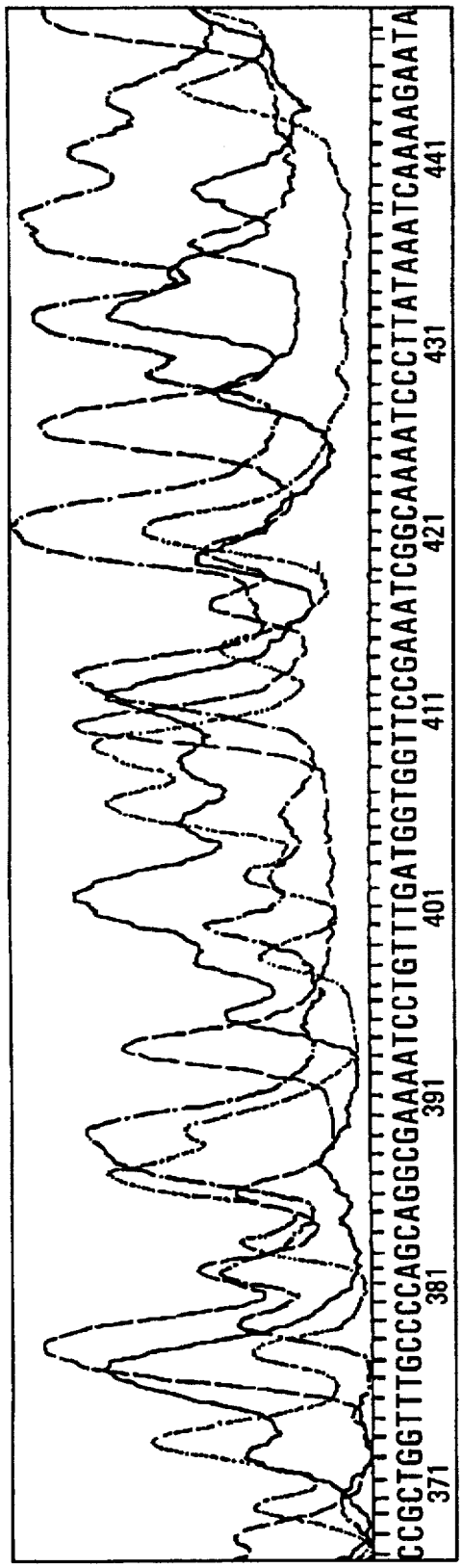
Figure 2H:
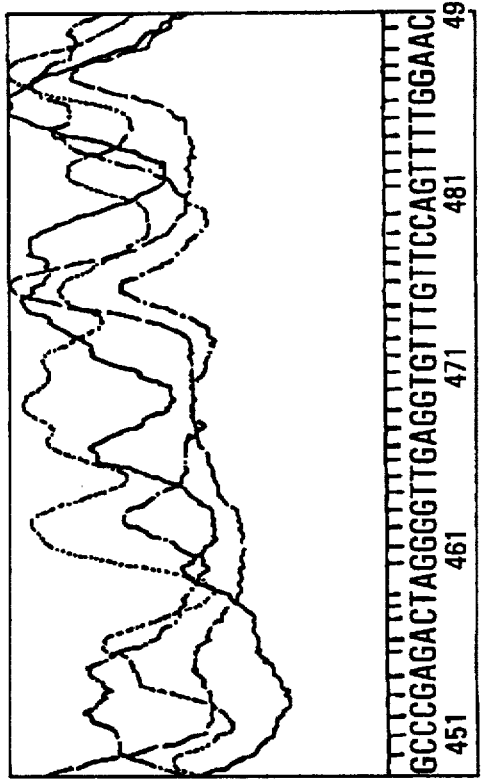

In a parallel experiment, a commercially available primer, eight bases longer (K-oligo), was used. In several experiments, depending on the purity or the shortmers used the reading distances with ligated primer reached from 80 to 100% of the reading distances obtained with a commercial primer (FIGS. 1 to 8).

I claim:

1. Process for the production of a primer for consecutive DNA sequencing, in which at least two shortmers are hybridised adjacent to one another using a template and are then ligated with one another to form the primer, the process being characterised in that
   (a) a template in the form of a single strand of nucleotides is used in which the number of nucleotides is at least 6 and is not greater than approximately twice the total number of nucleotides of the hybridising shortmers per template, and
   (b) the printer formed is then separated from the template and from unreacted shortmers and recovered.

2. Process according to claim 1 characterised in that the number of nucleotides in the templates is smaller by up to approximately the number of nucleotides in one of the shortmers used, or larger by up to approximately the number of nucleotides in one of the shortmers used, than the total number of nucleotides in the hybridising shortmers per template.

3. Process according to claim 1, characterised in that the number of nucleotides in the template corresponds approximately to the total number of nucleotides in the hybridising shortmers per template.

4. Process according to claim 1, characterised in that 6-mers, 7-mers, 8-mers and/or 9-mers arm used as shortmers.

5. Process according to claim 1, characterised in that two shortmers are used, it being possible for the number of nucleotides in the template to be from 8 to 18.

6. Process according to claim 1, characterised in that two shortmers
   (a) from a bank of (6-mers and/or 7-mers and/or
   (b) from a bank of 8-mers and/or 9-mers are used and, in the case of (a) and/or (b), an 8-mer or a 9-mer from a bank according to
   (b) is used as template.

7. Process according to claim 1, characterised in that a 5-mer is used with at least one shortmer from the group of the 7-mers, 8-mers or 9-mers.

8. Process according to claim 1, characterised in that a template or shortmers are used
   (a) that have inosine as nucleotide base or
   (b) in which A, C, G and/or T are present as nucleotide base(s) at the same position.

9. Process according to claim 1, characterised in that a template is used in which one of the nucleotide bases is labelled, for example radioactively or fluorescently, especially for the 3' end or the 5' end.

10. Process according to claim 1, characterised in that a template is used in which one of the nucleotide bases carries a radical for facilitating separation of the template, for example a biotin radical.

11. Process according to claim 1 characterised in that a template is used in which there is provided at at least one site a modified nucleotide base having exclusive complementarity that raises the melting temperature of a primer.

12. Bank (library) of templates, having up to $4^9$ mixtures of 10-, 11-, 12-, 13-, 14-, 15-, 16-, 17- or 18-mers that are suitable for the production of primers for consecutive DNA sequencing,
    two, three, four or more shortmers being hybridised adjacent to one another, using a template from the bank, to produce the primer,
    the hybridized shortmers then being ligated to form the primer and
    the primer formed then being separated from the template and from unreacted shortmers and recovered,
from at least one to a maximum of all of the nucleotides in from at least one template to all the templates in the bank having a complementarity similar to at least two of the four natural nucleotide bases, with the proviso that the total number of all conceivably possible templates in the bank does not exceed the total number of all shortmers conceivably possible for the production of the primer.

13. Bank according to claim 12, wherein nucleotides having a complementarity similar to at least two of the four natural bases are incorporated at one position or at individual positions of one, several or all of the templates.

14. Bank according to claim 13, wherein inosine is provided as a nucleotide having a complementarity similar to at least two of the four natural nucleotide bases.

15. Bank (library) of templates that are suitable for the production of primers for consecutive DNA sequencing,
    two, three, four or more shortmers being hybridised adjacent to one another, using a template from the bank, to produce the primer,
    the hybridised shortmers then being ligated to form the primer and
    the primer formed then being separated front the template and from unreacted shortmers and recovered,
the bank comprising up to $4^9$ mixtures of 10-, 11-, 12-, 13-, 14-, 15-, 16-, 17- or 18-mers, including 10-, 11-, 12-, 13-, 14-, 15-, 16-, 17- or 18-mers that are not present in a mixture, from two to four different bases complementary to the four natural bases being provided at one or at several positions of each of the templates of a mixture, with the proviso that the total number of all conceivably possible template mixtures, including templates from the bank that are not present in a mixture, does not in practice exceed the total number of all shortmers conceivably possible for the production of the primer.

16. Bank according to claim 15, wherein nucleotides having a complementarity similar to at least two of the four natural bases are incorporated at one position or at individual positions of one, several or all of the templates.

17. Bank according to claim 16, wherein inosine is provided as a nucleotide having a complementarity similar to at least two of the four natural nucleotide bases.

* * * * *